United States Patent [19]
Watson et al.

[11] Patent Number: 5,085,644
[45] Date of Patent: Feb. 4, 1992

[54] STERILIZABLE MEDICATION INFUSION DEVICE WITH DOSE RECHARGE RESTRICTION

[75] Inventors: David A. Watson, Goleta; Mark J. Licata, Santa Barbara, both of Calif.

[73] Assignee: Pudenz-Schulte Medical Research Corporation, Goleta, Calif.

[21] Appl. No.: 703,247

[22] Filed: May 20, 1991

Related U.S. Application Data

[63] Continuation-in-part of Ser. No. 679,658, Apr. 2, 1991, and a continuation-in-part of Ser. No. 503,426, Apr. 2, 1990.

[51] Int. Cl.⁵ .............................................. A61M 11/00
[52] U.S. Cl. .................................... 604/153; 604/185; 604/891.1; 604/93
[58] Field of Search ............. 604/93, 140, 153, 891.1, 604/890.1, 181, 183, 185, 186, 9; 128/DIG. 12

[56] References Cited

U.S. PATENT DOCUMENTS

| | | |
|---|---|---|
| 342,131 | 5/1886 | Perkins et al. . |
| 3,503,402 | 3/1970 | Schulte . |
| 3,527,220 | 9/1970 | Summers . |
| 3,756,243 | 9/1973 | Schulte . |
| 3,827,439 | 8/1974 | Schulte et al. . |
| 3,951,147 | 4/1976 | Tucker et al. . |
| 4,133,441 | 1/1979 | Mittleman et al. . |
| 4,360,019 | 11/1982 | Portner et al. . |
| 4,364,395 | 12/1982 | Redmond et al. . |
| 4,496,343 | 1/1985 | Prosl et al. . |
| 4,543,088 | 9/1985 | Bootman et al. . |
| 4,544,371 | 10/1985 | Dormandy, Jr. et al. . |
| 4,548,607 | 10/1985 | Harris .................................. 604/891.1 |
| 4,552,553 | 11/1985 | Schulte et al. . |
| 4,557,721 | 12/1985 | Hooven . |
| 4,557,722 | 12/1985 | Harris . |
| 4,559,033 | 12/1985 | Stephen et al. . |
| 4,560,375 | 12/1985 | Schulte et al. . |
| 4,588,394 | 5/1986 | Schulte et al. ........................... 604/9 |
| 4,634,424 | 1/1987 | O'Boyle . |
| 4,634,427 | 1/1987 | Hannula et al. . |

(List continued on next page.)

FOREIGN PATENT DOCUMENTS

664424 9/1965 Belgium .

OTHER PUBLICATIONS

Title: Implantable Devices for Drug Delivery to the Circulatory and Central Nervous Systems, Author: Robert H. Pudenz, M.D. 42 pages.
Title: N.Y.U. Volume Control Valve Drawing

*Primary Examiner*—Gene Mancene
*Assistant Examiner*—Michael Lynch
*Attorney, Agent, or Firm*—Kelly, Bauersfeld & Lowry

[57] ABSTRACT

A subcutaneously implantable medication infusion device includes a variable capacity reservoir for receiving and storing fluid medication for delivery to a catheter which directs the medication to a specific infusion location in the body. A control assembly is interposed between the reservoir and the catheter to facilitate and control the transfer of the medication from the reservoir to the catheter in a safe and efficient manner. The control assembly includes a self-recharging pump and a normally closed valve, both of which are manually actuable by percutaneous pressure when subcutaneously implanted, and a one-way valve positioned within a primary fluid conduit between the pump and the normally closed valve. The control assembly is constructed to permit the infusion of a measured bolus of medication on demand through manual percutaneous manipulation of the control assembly. A capillary-like fluid pathway through which the recharge fluid must pass before entering the pump, is provided to limit the rate the pump is recharged with medication, and to restrict the total amount of medication which can be pumped into the catheter over a given period of time. An alternate fluid conduit extends between the pump and the normally closed valve, and a Porex-type plug situated within the alternate fluid conduit prevents the flow of liquid medication therethrough under normal use conditions, but permits the passage of gasses through the alternate fluid conduit to facilitate steam autoclave sterilization of the pumping chamber.

32 Claims, 4 Drawing Sheets

U.S. PATENT DOCUMENTS

| | | |
|---|---|---|
| 4,673,394 | 1/1987 | Fenton, Jr. et al. |
| 4,681,560 | 7/1987 | Schulte et al. |
| 4,681,564 | 7/1987 | Landreneau |
| 4,681,570 | 7/1987 | Dalton |
| 4,685,905 | 8/1987 | Jeanneret nee Aab |
| 4,704,103 | 11/1987 | Stober et al. |
| 4,718,894 | 1/1988 | Lazorthes |
| 4,762,517 | 8/1988 | McIntyre et al. |
| 4,767,410 | 8/1988 | Moden et al. |
| 4,772,270 | 9/1988 | Wiita et al. |
| 4,781,680 | 11/1988 | Redmond et al. |
| 4,857,059 | 8/1989 | Rey et al. ............... 604/185 |
| 4,898,582 | 2/1990 | Faste |
| 4,898,583 | 2/1990 | Borsanyi et al. |
| 4,898,584 | 2/1990 | Borsanyi et al. |
| 4,898,585 | 2/1990 | Borsanyi et al. |
| 4,931,050 | 6/1990 | Idriss ............... 604/891.1 |

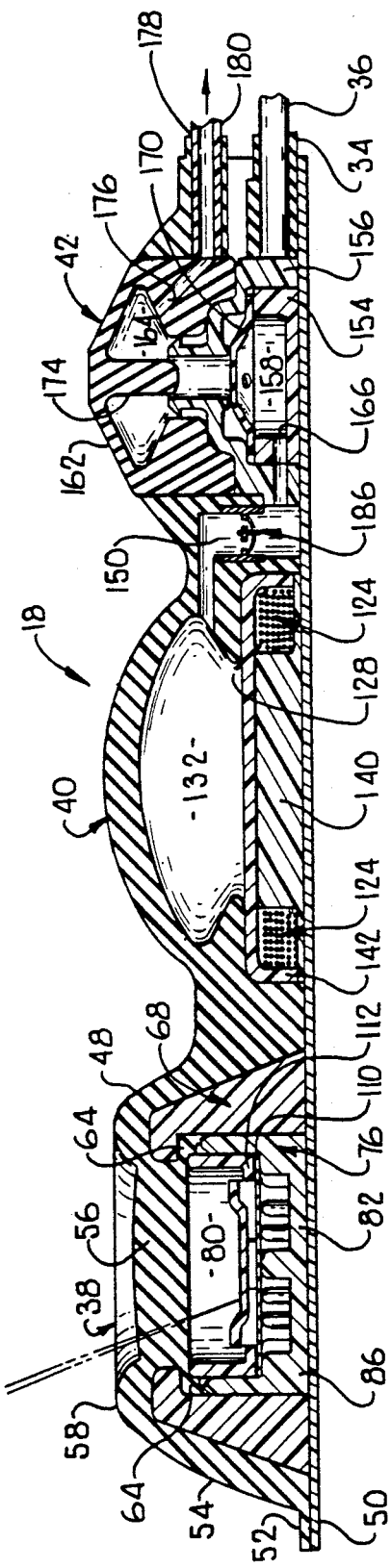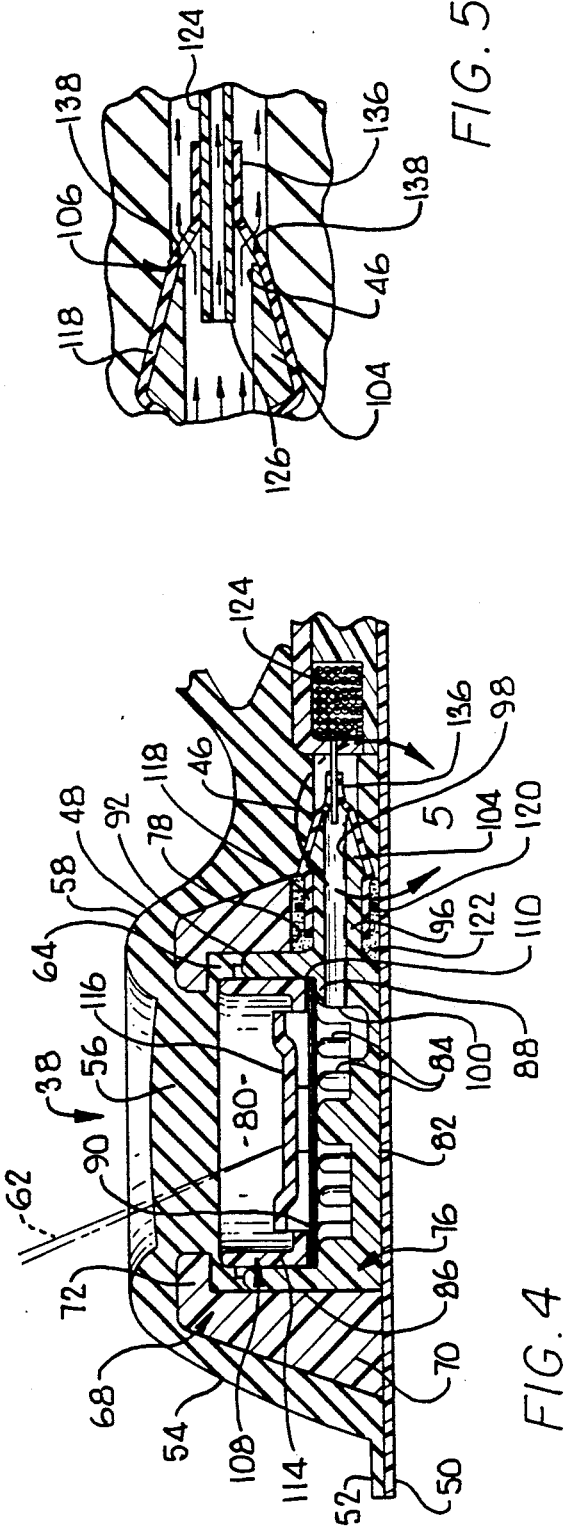

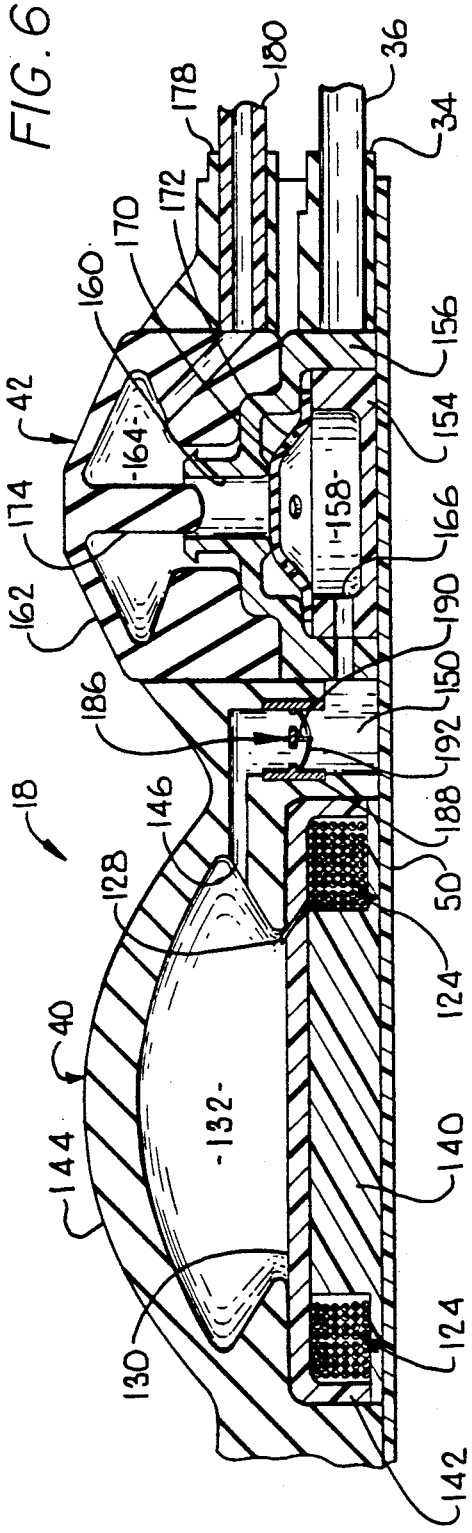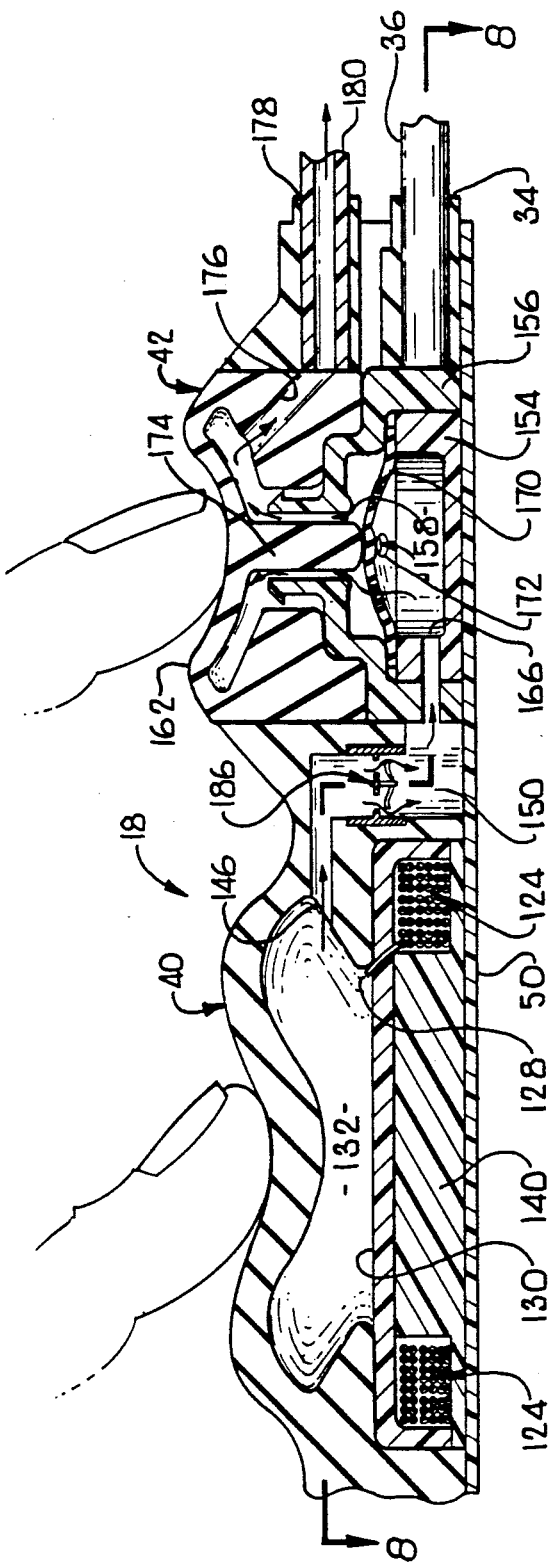

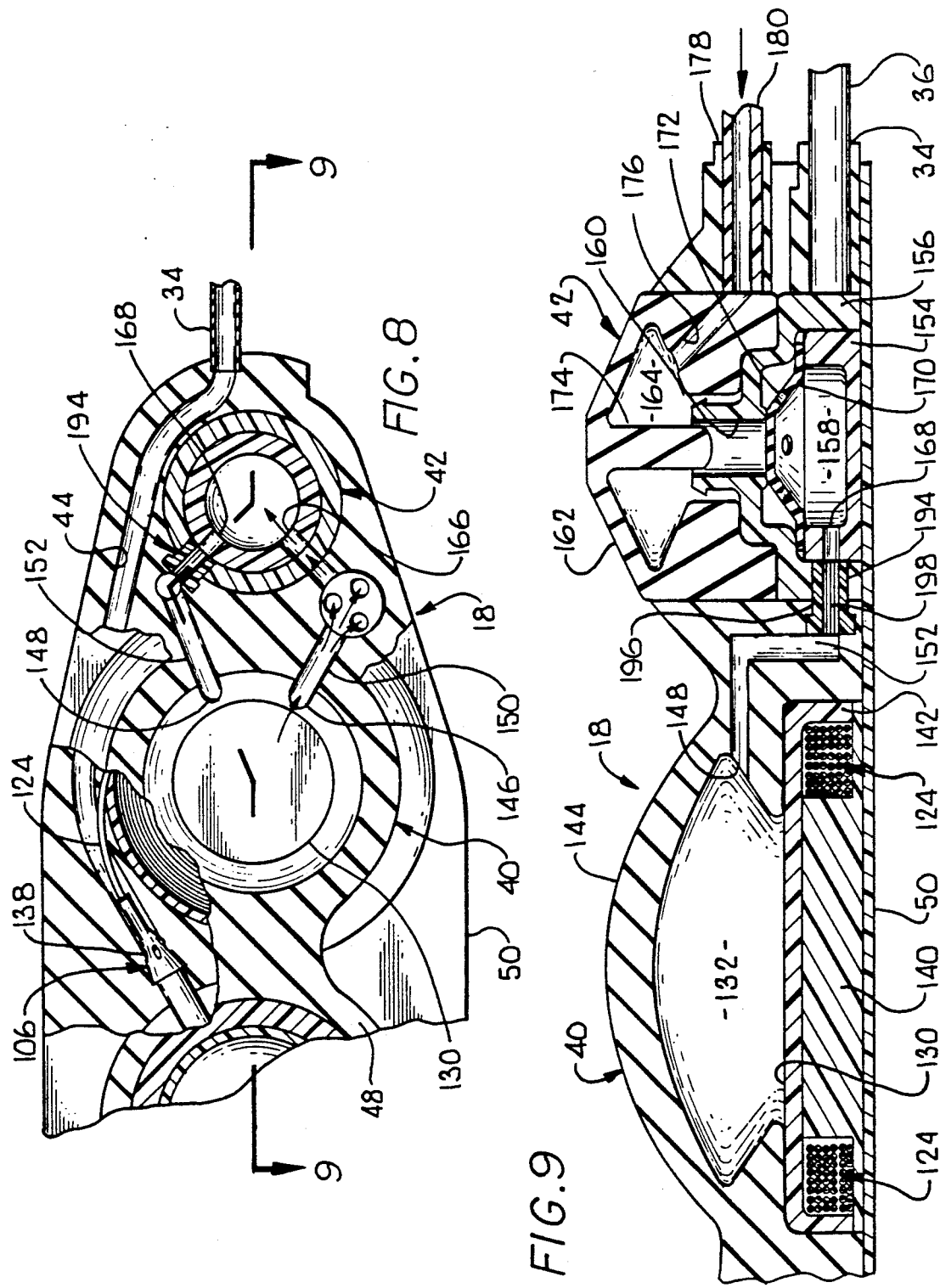

STERILIZABLE MEDICATION INFUSION DEVICE WITH DOSE RECHARGE RESTRICTION

RELATED APPLICATION

This is a continuation-in-part of U.S. Pat. application Ser. No. 07/679,658, filed Apr. 2, 1991 and entitled INJECTION PORT AND METHOD OF MANUFACTURE and U.S. Pat. application Ser. No. 07/503,426, filed Apr. 2, 1990 and entitled MEDICATION INFUSION DEVICE WITH DOSE RECHARGE RESTRICTION.

BACKGROUND OF THE INVENTION

This invention relates generally to infusion systems for the administration of medications. More particularly, the present invention relates to a refillable and subcutaneously implantable medication delivery system including means for limiting the total amount of medication which can be infused therethrough over a given period of time.

The administration of medications over sustained periods of time is necessary in the treatment of several various medical conditions. For instance, it is often desirable to provide a pain killer, such as morphine, to terminally ill patients to help them cope with the sometimes excruciating pain which accompanies certain diseases. Terminally ill patients frequently experience such extreme pain that hospitalization becomes necessary to provide medications at intervals and in quantities sufficient to meet the patient's needs. Alternatively, when hospitalization is not acceptable the patient is often required to obtain private nursing care.

Requiring a terminally ill patient to either be hospitalized or to arrange for private nursing care can become a substantial burden upon both the health care system and the patient. Health care facilities are increasingly burdened as the demand for hospital bed space increases at a rate greater than the growth in available bed space. This burden is accentuated when patients, such as terminally ill patients, are hospitalized for want of an alternative treatment methodology. Also, the diversion of medically trained personnel to deal with the routine infusion of medications imposes additional burdens on the health care system which could be avoided provided the proper technology were available.

When patients must be confined to a hospital bed or arrange for private duty nursing care to receive prescribed medications, the costs involved often exceed the financial means of such patients. For example, many terminally ill patients cannot afford to pay for the expensive and individualized care which could make the last period of time prior to death much more productive and less difficult for the patient and for those around him. Indeed, some patients cannot afford any medical care whatsoever and their only available alternative is to forego treatment. Sometimes patients who cannot afford the hospitalization or private nursing care required and who cannot tolerate the pain involved with a particular disease must be hospitalized at society's expense.

These burdens to the patient, the health care system and to society in general have prompted several changes in health care methodology. For instance, many physicians have found it desirable to administer prescribed medications on an outpatient basis. This outpatient technique has proven to be effective in substantially reducing the costs associated in the treatment of many types of ailments; however, there have been a number of drawbacks which have made such outpatient arrangements less than ideal.

A typical drawback of outpatient treatment programs involves the requirement of frequent visits by the patient with the physician and the resultant time and transportation problems. If the patient could be provided adequate home care for extended periods of time, the time between visits with the physician would be lengthened. Such extended home care would benefit the physician as well as the patient in many circumstances, by permitting the physician to devote more professional time to other important matters.

Notwithstanding the foregoing, some patients find that receiving regular injections of medication over a prolonged period of time is distasteful, not to mention painful. It has been found that repeated injections through the skin into a specific, limited area of the body can be harmful to the patient and can sometimes cause problems which could become more threatening to the well-being of the patient than the illness being treated. Such problems have made necessary the use of alternate injection sites, the rotation of injections among alternate injection sites, or, in the extreme, the abandonment of medication injections as a useful form of treatment. Moreover, some substances have been found to traumatize the skin when injected, and this has necessitated the use of alternative means for introducing such substances into the body. Such alternate introduction means have included the use of catheters which are inserted through the skin into the body and have a portion which remains extended through the patient's skin to provide external access. This and similar methods and systems have proven to be undesirable for extended treatment because of the risk of infection at the incision site where the catheter extends through the skin.

In an effort to overcome the above-noted drawbacks associated with prior treatment procedures, several types of drug delivery devices have been developed which permit the self-administration of medication in precise quantities while minimizing the number of injections required and visits which need be made with a physician. Exemplary of such prior drug delivery devices are those illustrated in U.S. Pat. Nos. 4,588,394 and 4,681,560, the contents of which are incorporated herein by reference. These prior systems are constructed for total subcutaneous emplacement in the body, include appropriate devices to prevent the unintended infusion of the medication from the system into the body, and are refillable by injection to permit long term use. Such devices may be useful not only in the administration of medication to terminally ill patients, but also in the administration of other medications, such as insulin to diabetic patients.

The development of infusion systems which are totally subcutaneously emplaced in the body and which are actuated by manual percutaneous manipulation, has caused some medical professionals to worry that such devices may pose a danger to the patient since the medication is self-administered. In the case of a terminally ill patient, there is a danger that the patient or another giving care to the patient may infuse too great a quantity of a substance such as morphine through the system, in the absence of suitable safeguards. Similarly, in the case of diabetic patients, there is a danger, or at least the possibility, that too great a quantity of insulin could be self-administered through implantable and manually actuable systems and devices.

In efforts to ensure that medication is not accidentally infused into the patient, prior implantable infusion systems are usually designed to require at least two positive percutaneous manipulative steps before medication is permitted to pass into a delivery catheter for infusion into the body. The above-referenced patents show good examples of prior devices incorporating such safeguards. Some medical professionals have opted not to give the patient the opportunity to self-administer medication, but regulate the rate of medication infusion through systems powered by internal batteries or external power sources.

Accordingly, there has been a need in the medical arts for implantable infusion systems which allow the patient to administer required medications in precise quantities while minimizing the number of injections required and visits which need be made with a physician. Such infusion systems are needed which inherently limit the amount of medication which can be infused into the patient over a given period of time. Preferably, such limitation on the total amount of medication which can be infused over a given period of time can be accomplished independently of the size of a reservoir for storing the medication. Further, a novel medication delivery device is needed which may be totally subcutaneously emplaced in the body, includes appropriate devices to prevent the unintended infusion of the medication from the system to the body, is refillable by injection to permit long-term use, and includes an inherent recharge restriction capability for limiting the rate at which medication may be infused to the body while preserving the ability of the patient to self-administer the medication on demand in a safe and reliable manner. Moreover, such a medication delivery device should be constructed to facilitate autoclave sterilization thereof, without limiting the desired characteristics of the device. The present invention fulfills these needs and provides other related advantages.

SUMMARY OF THE INVENTION

The present invention resides in a medication infusion device useful, for example, in the administration of medication to a patient requiring infusions of medication at relatively frequent intervals and over extended periods of time. More particularly, the present invention resides in a medication infusion system which is totally subcutaneously implanted in the patient, and is manually actuated by the application of percutaneous pressure to infuse a measured bolus of medication on demand. The infusion system comprises, generally, means for receiving medication into the system by injection, a reservoir fluidly connected to the receiving means in a manner permitting the subcutaneous transfer of medication from the receiving means to the reservoir, and a delivery catheter for directing the medication to a specific location in the body. Means are provided for conducting the medication from the reservoir to a catheter inlet. Further, means are provided for controlling the flow of medication from the reservoir to the catheter, forming a portion of the conducting means, which include a pump for flushing a measured quantity of medication from a pumping chamber, and valve means for controlling the flow of medication from the pumping chamber to the catheter. Additionally, means are provided for restricting the flow of medication from the reservoir to the pump, and thus limiting the rate the pump is recharged, to restrict the total amount of medication which can be pumped into the catheter over a given period of time. Moreover, means are provided for bypassing a portion of the conducting means within the controlling means, to permit steam autoclave sterilization of the pumping chamber through the valve means, and yet disallow the flow of liquid fluid through the bypassing means.

In a preferred form of the invention, the medication receiving means comprises an injection port including an elastomeric outer housing having an integral elastomeric septum, a first base member situated within the outer housing and contiguously engaging a peripheral flange of the septum, and a second base member situated within the first base member and the outer housing. The second base member contiguously engages the peripheral flange of the septum opposite the first base member such that the septum is compressed between the first and second base members. The second base member and the septum define an internal chamber. An outlet extends from the lower portion of the internal chamber exteriorly through the outer housing.

A filter barrier is supported by the second base member of the injection port, and separates the internal chamber into an upper portion adjacent to the septum and a lower portion. Means are provided for sealing an outer peripheral flange of the filter barrier adjacent to the second base member, to require any fluid injected into the upper portion of the internal chamber to pass through the filter barrier before passing through the outlet to exit the injection port. The sealing means includes a needle guard for preventing contact between a needle inserted through the septum into the internal chamber, and the filter barrier.

The means for sealing the outer peripheral flange of the filter barrier comprises a third base member which is cup-shaped and includes a filter barrier-engaging base, a continuous wall which extends upwardly therefrom, and a floor spaced from the filter barrier and supported by the base. The continuous wall engages an inner surface of the second base member in an interference fit. The third base member includes an upper septum-engaging section which extends upwardly from the continuous wall to underlie the peripheral flange of the septum and compress the peripheral flange of the septum between the first base member and the upper septum-engaging section of the third base member. A gasket is disposed between the third base member and the outer peripheral flange of the filter barrier.

The second base member of the injection port includes a floor having filter supports extending upwardly therefrom for supporting the filter barrier. The upwardly extending floor supports form a labyrinth passageway in open fluid communication with the outlet of the injection port.

The elastomeric outer housing of the injection port includes an upper dome attached to a lower reinforced sheet. The upper dome includes a lower flange sealed to the reinforced sheet, a frusto-conical side wall extending upwardly from the lower flange, and the septum which is integrally formed with the side wall and supported thereby in spaced relation to the lower reinforced sheet. The first base member comprises a generally frusto-conical ring configured to engage and support an interior surface of the side wall, and a rigid upper flange which overlies the peripheral flange of the septum to provide a rigid barrier between the peripheral flange of the septum and the adjacent side wall portions. The upper flange circumscribes the septum and engages the peripheral flange of the septum. The second base member is cup-shaped and includes a floor and a continuous wall which extends upwardly therefrom. The continuous wall projects from the floor to engage an inner surface of the first base member in an interference fit. This wall includes an upper septum-engaging section which underlies the peripheral flange of the septum and compresses it against the upper flange of the first base member.

The reservoir includes a flexible outer body capable of expanding to accommodate varying amounts of medication.

The pump includes a pump inlet in fluid communication with the reservoir, a pump outlet in fluid communication with the valve means, and a resilient crown overlying a floor plate to define the pumping chamber therebetween.

The valve means includes a normally closed valve actuable by manual percutaneous manipulation, wherein fluid is directed from the pumping chamber to the normally closed valve through a primary fluid conduit. The normally closed valve includes a resiliently flexible body which defines a fluid flow passageway therethrough, and a valve member positioned within the fluid flow passageway to occlude the normally closed valve. The normally closed valve further includes a valve inlet in fluid communication with the pump through the primary fluid conduit, a valve outlet in fluid communication with the catheter inlet, and a valve passageway situated directly between the valve inlet and the valve outlet. The valve member is resiliently biased to occlude the valve passageway, and a displacement finger is situated and configured within the valve to displace the valve member and open the normally closed valve to fluid flow therethrough when actuated by manual percutaneous pressure.

The valve means further includes a one-way valve which controls the passage of fluid through the primary fluid conduit.

The restricting means includes a capillary-like fluid pathway through which the medication must pass before entering the pump. The capillary-like fluid pathway comprises a length of capillary tubing wound about a spool and situated within a rigid housing, and having an inlet end in fluid communication with the reservoir and the medication receiving means, and an outlet end in fluid communication with the pumping chamber. The capillary tubing inlet is positioned within a bifurcation valve which permits medication to flow freely between the reservoir, the medication receiving means, and the capillary tubing inlet.

The bypassing means includes an alternate fluid conduit extending between the pumping chamber and the normally closed valve, and means for preventing the passage of liquid fluid through the alternate fluid conduit, and yet permitting the passage of gaseous fluid therethrough. The means for preventing the passage of liquid fluid through the alternate fluid conduit and yet permitting the passage of gaseous fluid therethrough, comprises a Porex-type plug.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 3 is an enlarged sectional view of the control assembly taken generally along the line 3—3 of FIG. 2, illustrating a discharge fluid pathway from a pump through a valve for infusion as directed by the catheter;

FIG. 4 is an enlarged fragmented sectional view taken generally along the line 4—4 of FIG. 2, illustrating the construction of an injection port portion of the control assembly, and the manner in which medication may be injected through a septum of the injection port;

FIG. 5 is an enlarged, fragmented sectional view of the portion of FIG. 4 designated by the line 5, illustrating a bifurcation valve positioned adjacent to the outlet of the injection port;

FIG. 6 is an enlarged fragmented sectional view of a portion of the control assembly taken generally along the line 3—3 of FIG. 2 illustrating, particularly, a discharge fluid pathway from the pump through the valve for infusion as directed by the catheter;

FIG. 7 is a fragmented sectional view of a portion of the control assembly similar to that illustrated in FIG. 6, illustrating the manner in which percutaneous pressure is utilized to open a normally closed valve and then flush discharged fluids from a pumping chamber within the pump;

FIG. 8 is a reduced fragmented sectional view taken generally along the line 8—8 of FIG. 7, illustrating alternate pathways extending between the pumping chamber and the normally closed valve, wherein a first of such pathways (a primary fluid conduit) is utilized as a portion of the discharge fluid pathway to direct fluid from the pumping chamber to the discharge catheter, and a second of such pathways (an alternate fluid conduit) is utilized during sterilization of the control assembly; and FIG. 9 is an enlarged fragmented sectional view taken generally along the line 9—9 of FIG. 8, illustrating the second pathway (the alternate fluid conduit) extending between the normally closed valve and the pumping chamber through which a gas is forced to sterilize the pumping chamber.

DETAILED DESCRIPTION OF THE PREFERRED EMBODIMENT

Figure 1:
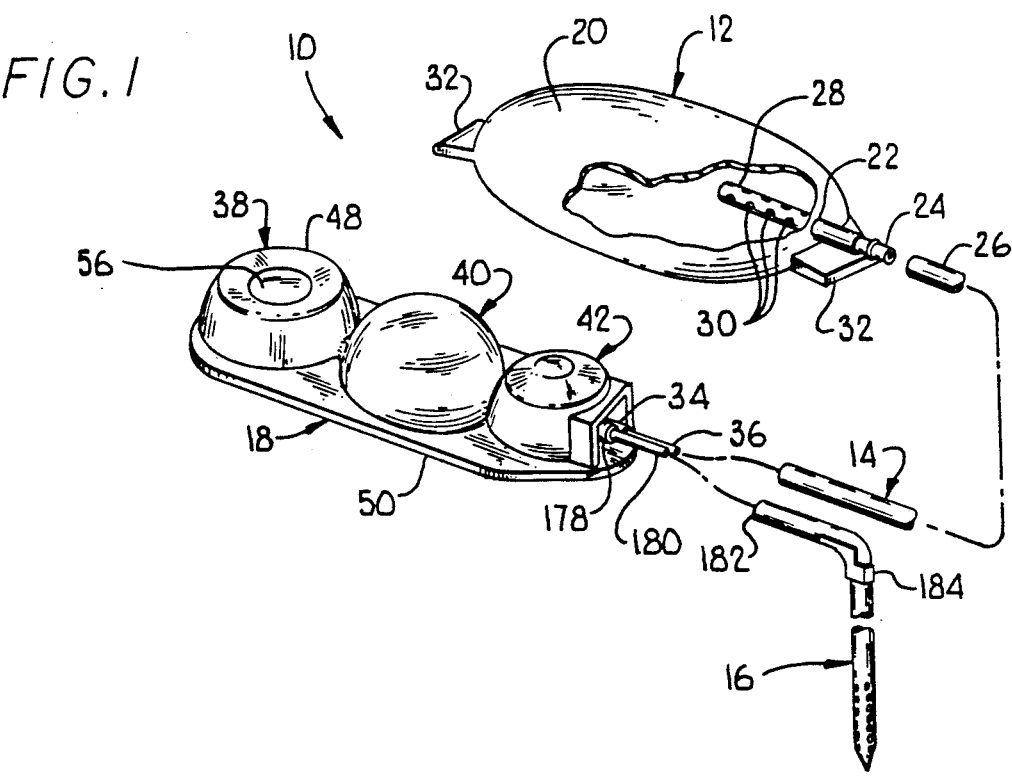
FIG. 1 is a partially fragmented perspective diagrammatic view of a preferred form of the sterilizable medication infusion device of the present invention, illustrating the relationship of the various components of the infusion device to one another, and specifically the relationship of a control assembly relative to a reservoir and a delivery catheter, wherein a portion of the reservoir shell is broken away for illustrative purposes only.
Figure 2:
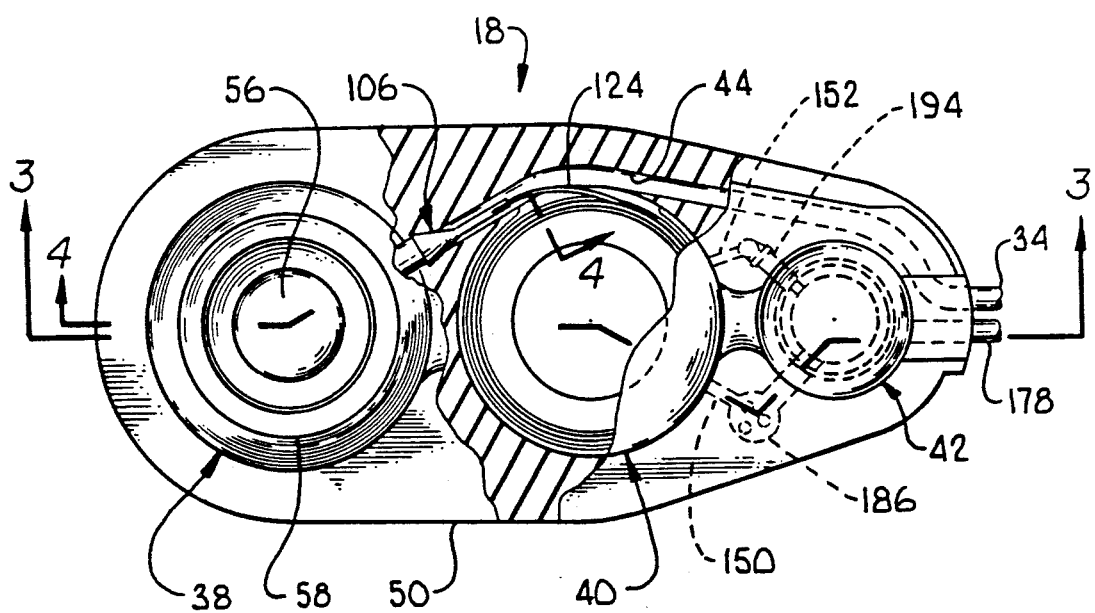
FIG. 2 is an enlarged, partially sectional top plan view of the control assembly illustrated in FIG. 1.

As shown in the drawings for purposes of illustration, the present invention is concerned with an improved medication infusion system, generally designated in the accompanying drawings by the reference number 10. As illustrated best in FIG. 1, the medication infusion system 10 generally comprises a variable capacity reservoir 12 connected by a fluid flow conduit 14 to a catheter 16 which directs medications stored in the reservoir to a specific location within a patient. A fluid flow control assembly 18 is provided to prevent or reduce the likelihood of an inadvertent infusion into the patient of medication stored in the reservoir 12.

The control assembly 18 used in the system 10 is situated between the reservoir 12 and the catheter 16 to form a portion of the fluid flow conduit 14. The system 10 requires fluid medication to flow through the control assembly 18 before passing into the catheter 16. With the safety and well-being of the patient an all-important consideration in the employment of the system 10, this flow path requirement provides the control over the flow of medication which is critical to the system's safe use. Indeed, the control assembly 18 virtually eliminates the chance of inadvertently infusing more than a very small quantity of medication into the patient by requiring specific sequential and deliberate steps to be taken before a measured volume of fluid can be pumped through the system 10.

The medication infusion system 10 can substantially reduce the cost of treating some illnesses by eliminating the need for constant medical attention or by reducing the number of required visits which need be made with a physician. The overall design of the system 10 permits construction into a variety of configurations for use in many types of different applications. The system 10 may be used advantageously by patients requiring regular infusions, by minimizing the number of injections received. As will be discussed in greater detail below, the medication infusion system 10 of the present invention includes means for limiting the maximum amount of medication which can be pumped through the system over a given time period.

In accordance with the present invention, the variable capacity reservoir 12 comprises a silicone elastomer shell 20 which can expand and collapse to accommodate changing volumes of fluid medication. The reservoir 12 includes an outlet aperture 22 and an outlet connector 24 secured within the aperture 22. The outlet connector 24 is designed to engage one end of a first segment of surgical tubing 26 which extends between the reservoir 12 and the control assembly 18.

A flexible tube 28 having a plurality of tube apertures 30 extends from the reservoir aperture 22 generally rearwardly into the center of the reservoir 12. The flexible tube 28 is preferably constructed of a silicone elastomer material having sufficient resiliency to maintain a fluid passageway through its center for channeling fluid medication from the reservoir 12 through the aperture 22 and into the first segment of surgical tubing 26, notwithstanding a collapse of the reservoir shell 20. Specifically, the flexible tube 28 ensures that fluid medication will be able to exit the reservoir 12 even when the reservoir shell 20 collapses in a manner that would otherwise occlude the reservoir outlet aperture 22. Such a collapse of the reservoir shell 20 may result from an emptying of fluid from the reservoir 12 during use of the system 10.

In systems 10 designed for use in the treatment of terminally ill patients, a reservoir 12 having a thirty milliliter capacity would normally hold sufficient amounts of morphine or other similar pain killing drugs to supply patients sufficient quantities of medication for several days. The variable capacity reservoir 12 can be remotely located from the insertion point of the catheter 16 in any suitable position as the surgeon chooses, such as in the abdominal cavity, below the ribs or near the clavicle. Indeed, the reservoir 12 can be placed in any soft area of the body which would permit the reservoir to be percutaneously grasped while subcutaneously implanted. To aid in the positioning of the reservoir 12, suture tabs 32 are integrally formed with the reservoir shell 20 to permit the surgeon to anchor the reservoir 12 at the selected location within the patient to prevent migration of the reservoir to an undesirable location.

The first segment of surgical tubing 26 extends from the outlet connector 24 of the reservoir 12, to a first port 34 of the control assembly 18. An end 36 of the surgical tubing 26 is fixed within the first port 34 in any suitable manner which prevents separation of the first segment of surgical tubing 26 from the control assembly 18.

The control assembly 18 includes three primary components: an injection port 38, a pump 40 and a normally closed valve 42. An injection port fluid outlet passageway 44 is provided through the control assembly 18 between an outlet 46 of the injection port 38, and the first port 34 of the control assembly.

The injection port 38 shown in the accompanying drawings (FIGS. 1 through 4) is constructed as part of the control assembly unit 18. The injection port 38, however, could be manufactured as a separate component apart from the pump 40 and the normally closed valve 42, since it does not directly interrelate with the function of the pump and the normally closed valve. The injection port 38 comprises an upper elastomeric dome 48, a lower elastomeric reinforced sheet 50, and a base structure housed within the dome above the reinforced sheet. The upper dome 48 includes a lower flange 52 which is directly sealed to the reinforced sheet 50 by means of a standard adhesive. Accordingly, the dome 48 and the reinforced sheet 50 present a continuous elastomeric outer housing for the injection port 38, which helps prevent leakage of drugs injected into the housing when the injection port is subcutaneously implanted.

Extending upwardly from the dome flange 52 is a frusto-conical side wall 54 which supports an integrally formed septum 56 in spaced relation above the lower reinforced sheet 50. The upper end of the side wall 54 surrounding the septum 56 provides means for percutaneously manually locating the septum when the injection port 38 is subcutaneously implanted. More particularly, the side wall 54 includes a ridge 58 which circumscribes an upper exterior surface of the septum 56. The dome 48 is provided with an outlet connector passageway through a lower portion thereof.

The septum 56 comprises a thickened portion of, preferably, a silicone elastomer material having characteristics which permit repeated, intermittent puncture by a needle 62 for injection of drugs. Such a needle 62 is preferably twenty-gauge or smaller. The septum 56 includes a peripheral flange 64 which generally circumscribes a lower end of the septum beneath the ridge portion 58 of the side wall 54. The peripheral flange 64 defines a flange-receiving cavity into which a portion of a first base member 68 is positioned.

The first base 68 is preferably formed of a rigid polypropylene material and includes a generally frusto-conical ring 70 configured to contiguously engage and support the interior surface of the dome side wall 54. The first base member 68 further includes a rigid upper flange 72 configured to fit within the flange receiving cavity of the dome 48, and circumscribe the septum 56 to engage the peripheral flange 64. More particularly, the rigid upper flange 72 of the first base member 68 overlies the peripheral flange 64 and provides a rigid barrier between the peripheral flange and the adjacent portions of the dome side wall 54.

Below the rigid upper flange 72 of the first base member 68, the interior of the ring-like side wall 70 forms an inner cylindrical surface which is dimensioned to receive and firmly hold a second base member 76 in an interference fit therein. The first base member 68 includes an outlet connector passageway 78 in the lower end of the ring 70, which is aligned with the outlet connector passageway of the elastomeric dome 48.

The second base member 76 is preferably formed of a rigid polypropylene material and when positioned within the first base member 68, defines, with the septum 56, an internal injection chamber 80. The second base member 76 is generally cup-shaped and includes a floor 82 having a plurality of upwardly extending filter supports 84, and a continuous cylindrical wall 86 which extends upwardly from the floor 82. The wall 86 includes a step 88 spaced the same distance from the floor 82 as the upper ends of the filter supports 84, to provide an outer peripheral supporting surface for a filter barrier 90. An upper septum-engaging section 92 extends upwardly from the upper end of the continuous wall 86 and, in the assembled configuration, engages the underside of the peripheral flange 64. The upper septum-engaging section 92 meets the continuous wall 86 at a shoulder, and is positioned relative to the first base member 68 so as to compress the septum peripheral flange 64 between the section 92 and the rigid upper flange 72. This creates a fluid-tight seal between the base members 68 and 76, on the one hand, and the septum 56 on the other, and further tends to improve the resealing characteristics of the septum.

An outlet is provided the injection port 38, which extends from the injection chamber 80 exteriorly through the first and second base members 68 and 76, to a point outside of the elastomeric dome 48. More specifically, the outlet includes a rigid outlet connector 96 which, preferably, is integrally formed with the second base member 76. The outlet connector 96 provides a fluid conduit 98 which extends from an inlet port 100 situated on an interior surface of the second base member 76, to the outlet port 46 situated at a distal end of the outlet connector 96. Adjacent to the outlet port is a tapered portion 104 which is configured to receive a portion of a bifurcation valve 106 (FIGS. 4 and 5).

The filter barrier 90 extends across the injection chamber 80 and rests atop the filter supports 84 and the wall step 88 provided by the second base member 76. In this manner, the filter barrier separates the injection chamber 80 into an upper portion adjacent to the septum 56, and a lower portion which is in open fluid communication with the fluid conduit 98 through the outlet connector 96. The outer peripheral flange of the filter barrier 90 is positioned directly over the wall step 88, and is secured in place by means of a third base member 108. Preferably, the filter barrier comprises a two-tenths micron filter.

An elastomeric gasket 110 is placed over the outer peripheral flange of the filter barrier 90 and is compressed between the wall step 88 of the second base member 76, and an overlying base 112 of the third base member 108. This effectively provides a means for sealing the outer peripheral flange of the filter barrier 90 adjacent to the second base member 76, to require any fluid injected into the upper portion of the injection chamber 80 to pass through the filter barrier before exiting the injection port 38. The third base member 108 provides a needle guard which prevents contact between the needle 62 inserted through the septum 56 into the injection chamber 80, and the filter barrier 90.

The third base member 108 is preferably formed of a rigid polypropylene material and is generally cup-shaped. The third base member 108 includes the filter barrier-engaging base 112, a continuous cylindrical wall 114 which extends upwardly from the base 112, and a floor 116 spaced from the filter barrier 90 and supported by the base 112. A passageway is provided between the base 112 and the floor 116 to permit fluid flow past the third base member 108 from the upper portion of the injection chamber 80, through the filter barrier 90, and into the lower portion thereof. The continuous wall 114 of the third base member 108 is configured to substantially contiguously engage an inner surface of the wall 86 of the second base member 76 in an interference fit. The upper end of the continuous wall 114 forms an upper septum-engaging section which engages the underside of the septum peripheral flange 64 in much the same manner as the section 92 of the second base member 76. The upper end of the wall 114 is positioned relative to the first base member 68 so as to compress the septum 56 between the upper end of the wall 114 and the rigid upper flange 72.

A sleeve portion 118 of the bifurcation valve 106 is placed over the outlet connector 96 to be positioned within the outlet connector passageway of the upper dome 48 and the passageway 78 of the first base member 68. The sleeve portion 118 is secured in place by means of a suture 120. The gap between the sleeve portion 118 and the dome 48 is filled with a silicone adhesive 122.

An open fluid conduit link is provided by the first segment of surgical tubing 26 and the injection port fluid outlet passageway 44 through the control assembly 18, to permit the free passage of medication injected into the injection chamber 80 to the reservoir 12. A recharge fluid flow passageway provides means for conducting pump recharge fluid from either the injection port 38 or the reservoir 12 to the pump 40. The recharge passageway includes means for restricting the rate of fluid flow through the recharge passageway, which effectively limits the amount of recharge fluid permitted to enter the pump over a given period of time.

In the illustrated embodiment, the recharge passageway is provided by a length of capillary tubing 124 having an inlet end 126 positioned within the outlet port 46 of the injection port 38, and an outlet end 128 which extends through a rigid floor plate 130 of the pump 40 into a pumping chamber 132. The inlet end 126 of the capillary tubing 124 is held within the outlet port 46 of the outlet connector 96 by the bifurcation valve 106. The bifurcation valve 106 comprises the outer sleeve portion 118 fitted over the outlet connector 96 adjacent to the outlet port 46, and an inner sleeve 136 positioned adjacent to the outlet port 46 of the injection port 38. The inlet end 126 of the capillary tubing 124 is securely fixed within the inner sleeve portion 118, and apertures 138 are provided through the outer sleeve adjacent to the inner sleeve 136 to permit fluid medication to flow freely between the reservoir 12 and the injection port 38, as well as with the inlet end 126 of the capillary tubing 124 (see FIG. 5).

The capillary tubing 124 is wound about a spool 140 and positioned, with the spool, within a spool cover 142. A portion of the spool cover 142 forms the pump floor plate 130. An aperture is provided through the spool cover 142 to permit the capillary tubing 124 to extend from the bifurcation valve 106 to the spool 140 (FIGS. 4 and 8).

The pump 40, which can receive fluids from either the reservoir 12 or the injection port 38 through the capillary tubing 124, comprises a resiliently flexible crown 144 integrally formed with the dome 48 of the injection port 38. The lower sheet 50 extends below all three primary components of the control assembly 18, and the spool 140 is disposed between the reinforced sheet 50 and the spool cover 142. The pumping chamber 132 is defined between the crown 144 and the pump floor plate 130, and preferably has an evacuation capacity of one milliliter. Importantly, for purposes of the embodiment shown, the crown 144 is resiliently biased to generally maintain a dome or arch-shape, but can be deformed to lie substantially flat against the floor plate 130. The volume of the pumping chamber 132 can be customized to accommodate various intended uses for the system 10 and the required dosage to be infused into the patient per pumping stroke. By constructing the crown 144 of the same material as the septum 56, medication can be injected, if necessary, directly into the pumping chamber 132. In this case, the floor plate 130 functions as a needle guard, and the puncture site will tend to close upon itself and seal when the needle 62 is removed. The pump 40 further includes two pump outlets 146 and 148 in fluid communication with, respectively, a primary fluid conduit 150 and an alternate fluid conduit 152, both of which place the pumping chamber 132 in fluid communication with the normally closed valve 42.

The normally closed valve 42 includes a rigid diaphragm support 154 adjacent to the underlying lower reinforced sheet 50. A rigid diaphragm cap/valve housing 156 overlies and surrounds the diaphragm support 152 and defines, with the diaphragm support, an inlet chamber 158 and a valve passageway 160 (formed by the valve housing 156). a resiliently flexible valve dome 162 is situated over the valve housing 156 to define, with the housing 156, an outlet chamber 164 which overlies the inlet chamber 158. The valve passageway 160 provides a fluid flow pathway between the inlet chamber 158 and the outlet chamber 164. The valve dome 162 is fixed within an extension of the elastomeric material forming the dome 48 of the injection port and the crown 144 of the pump 40. The diaphragm support 154 and the valve housing 156 each have aligned apertures which form inlets 166 and 168 for the normally closed valve 42. The first inlet 166 directs fluid from the primary fluid conduit 150 into the valve inlet chamber 158. The second inlet 168 provides a passageway between the alternate fluid conduit 152 and the inlet chamber 158.

A resiliently flexible valve diaphragm 170, constructed to form a dome-shaped member, is seated circumferentially upon the diaphragm support 154 within the inlet chamber 158 so that a portion of the diaphragm is normally positioned adjacent to the valve passageway 160. The valve diaphragm 170 has a plurality of diaphragm apertures 172. Unless forceably displaced away from the portion of the valve housing 156 surrounding the valve passageway 160, the diaphragm 170 forms a seal which prevents any fluid flow through the normally closed valve 42. It is preferred that the valve housing 156 and the diaphragm 170 be constructed of materials which do not stick to one another, particularly after long periods of storage.

A portion of the valve dome 162 overlying the outlet chamber 164 includes a downwardly extending diaphragm displacement finger 174 positioned directly above the valve passageway 160. The displacement finger 174 is situated for travel through the valve passageway 160 when pressed downwardly, and the diameter of the finger is small enough to prevent occlusion of the valve passageway 160 when the finger is pressed therethrough. When enough pressure is applied, the finger 174 causes the valve diaphragm 170 to flex downwardly a sufficient distance to break the valve seal and allow fluid to pass through the valve passageway 160 (FIG. 7). The valve dome 162 and the diaphragm 170 are each sufficiently resilient to return to their normal configurations and, consequently, close the normally closed valve 42 to fluid flow when the deforming pressure is removed. The inclusion of such a normally closed valve 42 in the system 10 enhances the system's utility and safety by preventing the flow of fluid through a discharge fluid flow conduit, partially defined by the normally closed valve 42, in the absence of direct, selectively applied percutaneous pressure on the control assembly 18.

A valve outlet passageway 176 directs fluids from the outlet chamber 164 to a second control assembly port 178. Fixed within the second port 178 is a second segment of surgical tubing 180 which conducts fluids discharged from the pumping chamber 132 from the control assembly 18 to the catheter 16.

The catheter 16 is preferably formed of a barium-impregnated silicone elastomer material which is radiopaque for detection by X-ray photography. A catheter inlet 182 is attached to the second segment of surgical tubing 180, and fluid medication exiting the control assembly 18 is directed by the catheter 16 for infusion into a specific portion of the body. For example, in the case of terminally ill patients a catheter 16 can be inserted into the lateral ventricle of the patient's brain. When such catheter placement is contemplated, a catheter clip 184, as shown in FIG. 1, can be advantageously utilized to hold the catheter 16 in place adjacent to a burr hole through the skull.

Although the injection port 38, the pump 40 and the normally closed valve 42 are shown in the exemplary drawings as combined to form the unitary control assembly 18, each component may be separately constructed to form individual system components which can be connected to one another by a fluid conduit such as flexible surgical tubing.

As mentioned previously, the primary fluid conduit 150 channels fluid medication from the first pump outlet 146 to the first valve inlet 166. A one-way valve 186 is positioned within the primary fluid conduit 150 to ensure that there is no backflow of fluid from the normally closed valve 42 into the pumping chamber 132. The one-way valve 186 is similar to the one-way valves illustrated and described in detail in U.S. Pat. No. 4,867,740. The one-way valve comprises a rigid cylindrical housing 188, a rigid nail 190 supported by the housing 188, and a flexible valve membrane 192 supported by the nail and forming a seal with a portion of the housing 188. The valve membrane 192 is configured to provide a minimal level of resistance to fluid flow through the primary fluid conduit 150 as indicated by the arrows in FIG. 7, and yet prevent reverse fluid flow therethrough.

As shown best in FIGS. 8 and 9, the alternate fluid conduit 152 extends between the second pump outlet 148 and the second valve inlet 168. A Porex plug 194 is positioned within a portion of the alternate fluid conduit 152, to prevent the passage of liquid fluid through the alternate conduit and yet permit the passage of gaseous fluid therethrough. As shown in the drawings, the Porex plug 194 includes a plug housing 196 positioned within a lower portion of the alternate fluid conduit 152 and extending into the valve housing 156. The plug housing 196 contains a fine filter material 198 which clogs on contact with liquids to disallow the passage of liquid fluids therethrough, but is porous enough to permit the passage of gaseous fluids, such as steam, therethrough. By positioning the Porex plug 194 between the pumping chamber 132 and the valve inlet chamber 158, liquid medication is prevented from entering into the normally closed valve 42 through the second valve inlet 168. Rather, all of the liquid medication flushed from the pumping chamber 132 is caused to pass through the primary fluid conduit 150 for entry into the normally closed valve 42 at the first inlet 166.

In use, the medication infusion system 10 provides a convenient means for percutaneously controlling the flow of fluid through the subcutaneously implanted infusion system, and yet includes important safety features which prevent the inadvertent, accidental infusion of medication, and further limits the maximum amount of medication which can be infused through the system over a given time period. To use the system 10, it must first be subcutaneously implanted. Preferably, the control assembly 18 is placed over a hard boney surface to provide sufficient resistance to percutaneous pressure which will be applied thereto. Often, when initially implanted, the system 10 has previously been primed with a sterile saline solution which must be evacuated and replaced with the desired medication.

Medication is introduced into the infusion system 10 through injection into the injection chamber 80 of the injection port 38. Medication injected into the injection chamber 80 flows through the injection port outlet fluid conduit 98 to the bifurcation valve 106. Here the injected medication will take the path of least resistance to either fill the reservoir 12 or the pumping chamber 132. When filling the reservoir 12, the fluid medication flows out of the control assembly 18 through the first control assembly port 34, through the first segment of surgical tubing 26 connecting the control assembly to the reservoir, and through the outlet connector 24 fixed within the reservoir aperture 22.

If the pump crown 144 has been depressed to flush priming fluid from the pumping chamber 132, it will attempt to regain its original dome shape since the crown is resiliently biased towards its original dome-like configuration. This creates a pressure differential which draws medication through the recharge fluid flow passageway from either the injection chamber 80 or the reservoir 12. Utilization of polymide capillary tubing 124 as the recharge fluid flow passageway, provides a flow restrictor which effectively limits the rate at which the pumping chamber 132 is permitted to draw-in recharge fluids. Preferably, the capillary tubing 124 allows the pumping chamber 132 to be recharged at a selected rate between 0.25 and 1.0 milliliters per hour. The one-way valve 186 within the primary fluid conduit 150 ensures that the pumping chamber 132 is recharged only with liquid medication being drawn through the inlet end 126 of the capillary tubing 124 located in the bifurcation valve 106, regardless of the state of the normally closed valve 42.

To begin the infusion of medication to the patient through the system 10, the normally closed valve 42 must be opened by applying percutaneous pressure thereto, to permit medication in the pumping chamber 132 to be discharged through the first pump outlet 146. The normally closed valve 42 is opened by manually applying percutaneous downward pressure to the valve dome 162 (FIG. 7). Such downward percutaneous pressure forces the displacement finger 174 downwardly through the valve passageway 160 to disengage the valve diaphragm 170 from the valve seat. Thus, by simply pressing downwardly on the valve dome 162, a discharge fluid conduit is opened through the valve 42 to permit medication to be flushed from the pump 40. When utilizing the capillary tubing 124 as illustrated, there is no need to simultaneously occlude the recharge passageway in order to prevent fluid flow out through the pump inlet, defined by the outlet end 128 of the capillary tubing 124. Because the capillary tubing 124 is so restrictive to fluid flow therethrough, it is only possible to force a very minute quantity of medication within the pumping chamber 132 into the outlet end 128 when depressing the pump crown 144, regardless of the downstream fluid pressure against which the pump 40 works.

With the normally closed valve 42 opened, medication in the pumping chamber 132 can be discharged through the first pump outlet 146, the primary fluid conduit 150 and the normally closed valve 42, by applying downward percutaneous pressure to the pump 40. This is accomplished by simply pressing the pump crown 144 downwardly to collapse the pump crown against the floor plate 130. Medication within the pumping chamber 132 is caused to flow from the pumping chamber 132 through the normally closed valve 42 to the second control assembly port 178, and into the second segment of surgical tubing 180 for delivery to the catheter 16.

After the medication is flushed from the pumping chamber 132, the normally closed valve 32 is closed by simply removing the percutaneous pressure applied thereto. The pump crown 144 thereafter attempts to regain its original dome-shaped configuration, drawing recharge fluid into the pumping chamber 132 at a rate controlled solely by the cross-sectional diameter and length of the capillary tubing 124.

As set forth above, the alternate fluid conduit 152 is not utilized to conduct fluid medication during normal operation of the control assembly 18. The alternate fluid conduit 152 is provided for the important purpose of providing a mechanism by which the control assembly 18, and particularly the pumping chamber 132, can be suitably sterilized prior to implantation in the patient.

It is well known in the medication arts to sterilize implantable articles utilizing steam autoclave sterilization techniques. Sterilization of the pumping chamber 132 utilizing such techniques would not be possible, however, without providing the alternate fluid conduit 152, since the one-way valve 186 would prohibit the passage of any liquid or gaseous fluids through the primary fluid conduit 150 into the pumping chamber. Further, because of the highly restrictive flow characteristics of the capillary tubing 124, sufficient steam could not be injected into the pumping chamber 132 through the capillary tubing to effect the desired sterilization of the pump 40. The Porex plug 194 situated within the alternate fluid conduit 152 does permit gaseous fluids, such as steam, to pass therethrough during the sterilization process. Accordingly, a direct link is provided between the inlet chamber 158 of the normally closed valve 42 and the pumping chamber 132 for such purposes. However, as described above, the Porex plug includes filter material 198 which disallows the passage of liquid fluids therethrough, thereby forming an effective barrier against the passage of liquid medication through the alternate fluid conduit during normal operation of the control assembly 18.

The medication infusion system 10 described above can greatly ease the burden of medical personnel and hospital facilities by providing means for internally storing a large quantity of medication which is to be administered to a patient over an extended period of time. Moreover, various device can be added to the system 10 for a multitude of purposes, such as the provision of a burr hole reservoir situated adjacent to the skull to facilitate injection of medications directly into the brain.

Although a particular embodiment of the invention has been described in detail for purposes of illustration, various modifications may be made without departing from the spirit and scope of the invention. Accordingly, the invention is not to be limited, except as by the appended claims.

We claim:

1. A fluid control assembly, comprising:
   a self-recharging, manually actuable pump for discharging a measured amount of fluid from a pumping chamber;
   means for conducting pump recharge fluid into the pumping chamber;
   means for conducting discharge fluid from the pumping chamber;
   valve means for controlling the flow of discharge fluid from the pumping chamber, the valve means forming a portion of the discharge fluid conducting means;
   an alternate fluid conduit extending between the pumping chamber and a portion of the discharge fluid conducting means within the valve means; and
   means for preventing the passage of liquid fluid through the alternate fluid conduit, and yet permitting the passage of gaseous fluid therethrough.

2. A fluid control assembly as set forth in claim 1, wherein the pump includes a pump inlet in fluid communication with the recharge fluid conducting means, a pump outlet in fluid communication with the discharge fluid conducting means, and a resilient crown overlying a floor plate to define the pumping chamber therebetween.

3. A fluid control assembly as set forth in claim 1, including means for restricting the rate of fluid flow through the recharge fluid conducting means, wherein the restricting means limits the amount of recharge fluid permitted to enter into the pumping chamber over a given period of time.

4. A fluid control assembly as set forth in claim 3, wherein the restricting means includes at least one capillary-like fluid pathway through which the recharge fluid must pass before entering the pumping chamber.

5. A fluid control assembly as set forth in claim 1, wherein the valve means includes a normally closed valve actuable by manual percutaneous manipulation, and wherein fluid is directed from the pumping chamber to the normally closed valve through a primary fluid conduct.

6. A fluid control assembly as set forth in claim 5, wherein the normally closed valve includes a resiliently flexible body which defines a fluid flow passageway therethrough, a valve member positioned within the fluid flow passageway to occlude the valve means, a valve inlet in fluid communication with the primary fluid conduit, a valve outlet, and a valve passageway situated between the valve inlet and outlet, wherein the valve member is resiliently biased to occlude the valve passageway.

7. A fluid control assembly as set forth in claim 6, wherein the normally closed valve includes a displacement finger which is situated and configured to displace the valve member and open the normally closed valve to fluid flow therethrough when the normally closed valve is actuated by manual percutaneous manipulation.

8. A fluid control assembly as set forth in claim 5, wherein the valve means further includes a one-way valve controlling passage of fluid through the primary fluid conduit.

9. A fluid control assembly as set forth in claim 5, wherein the alternate fluid conduit extends between the pumping chamber and the normally closed valve.

10. A fluid control assembly as set forth in claim 1, wherein the means for preventing the passage of liquid fluid through the alternate fluid conduit, and yet permitting the passage of gaseous fluid therethrough, comprises a Porex-type plug.

11. An infusion reservoir and pump system, comprising:
    means for receiving medication into the system by injection;
    a reservoir fluidly connected to the receiving means in a manner permitting the subcutaneous transfer of medication from the receiving means to the reservoir;
    a catheter for directing the medication to a specific location in a body, the catheter having a catheter inlet and being positionable within the body independently of the position of the reservoir;
    means for conducting the medication from the reservoir to the catheter inlet;
    means for controlling the flow of medication from the reservoir to the catheter, the controlling means forming a portion of the conducting means and including a pump for flushing a measured quantity of medication from a pumping chamber, and valve means for controlling the flow of medication from the pumping chamber to the catheter;
    means for restricting the flow of medication from the reservoir to the pump, and thus limiting the rate the pump is recharged, to restrict the total amount of medication which can be pumped into the catheter over a given period of time; and
    means for bypassing a portion of the conducting means within the controlling means, the bypassing means permitting steam autoclave sterilization of the pumping chamber through the valve means, and yet disallowing the flow of liquid fluid through the bypassing means.

12. A system as set forth in claim 11, wherein the means for receiving medication into the system by injection comprises an injection port including an elastomeric outer housing having an integral elastomeric septum, a first base member situated within the outer housing and contiguously engaging a peripheral flange of the septum, a second base member situated within the first base member and the outer housing, the second base member contiguously engaging the peripheral flange of the septum opposite the first base member such that the septum is compressed between the first and second base members, wherein the second base member and the septum define an internal chamber, and an outlet extending from the lower portion of the internal chamber exteriorly through the outer housing.

13. A system as set forth in claim 12, wherein the injection port includes a filter barrier supported by the second base member and separating the internal chamber into an upper portion adjacent to the septum and a lower portion, and means for sealing an outer peripheral flange of the filter barrier adjacent to the second base member, to require any fluid injected into the upper portion of the internal chamber to pass through the filter barrier before passing through the outlet to exit the injection port, wherein the sealing means includes a needle guard for preventing contact between a needle inserted through the septum into the internal chamber, and the filter barrier.

14. A system as set forth in claim 12, wherein the elastomeric outer housing includes an upper dome attached to a lower reinforced sheet, the upper dome including a lower flange sealed to the reinforced sheet, a frusto-conical side wall extending upwardly from the lower flange, and the septum which is integrally formed with the side wall and supported thereby in spaced relation to the lower reinforced sheet, the first base member comprising a generally frusto-conical ring configured to engage and support an interior surface of the side wall, and a rigid upper flange which overlies the peripheral flange of the septum to provide a rigid barrier between the peripheral flange of the septum and the adjacent side wall portions, wherein the upper flange circumscribes the septum and engages the peripheral flange of the septum.

15. A system as set forth in claim 14, wherein the second base member is cup-shaped and includes a floor and a continuous wall which extends upwardly therefrom, wherein the continuous wall projects from the floor to engage an inner surface of the first base member in an interference fit, the wall including an upper septum-engaging section which underlies the peripheral flange of the septum and compresses the peripheral flange of the septum against the upper flange of the first base member.

16. A system as set forth in claim 11, wherein the reservoir includes a flexible outer body capable of expanding to accommodate varying amounts of medication.

17. A system as set forth in claim 11, wherein the pump includes a pump inlet in fluid communication with the reservoir, a pump outlet in fluid communication with the valve means, and a resilient crown overlying a floor plate to define the pumping chamber therebetween.

18. A system as set forth in claim 11, wherein the valve means includes a normally closed valve actuable by manual percutaneous manipulation, and wherein fluid is directed from the pumping chamber to the normally closed valve through a primary fluid conduit.

19. A system as set forth in claim 18, wherein the normally closed valve includes a resiliently flexible body which defines a fluid flow passageway therethrough, a valve member positioned within the fluid flow passageway to occlude the normally closed valve, a valve inlet in fluid communication with the pump through the primary fluid conduit, a valve outlet in fluid communication with the catheter inlet, and a valve passageway situated directly between the valve inlet and the valve outlet, wherein the valve member is resiliently biased to occlude the valve passageway.

20. A system as set forth in claim 19, wherein the normally closed valve includes a displacement finger which is situated and configured to displace the valve member and open the normally closed valve to fluid flow therethrough when the normally closed valve is actuated by manual percutaneous manipulation.

21. A system as set forth in claim 18, wherein the valve means further includes a one-way valve controlling controlling passage of fluid through the primary fluid conduit.

22. A system as set forth in claim 18, wherein the bypassing means includes an alternate fluid conduit extending between the pumping chamber and the normally closed valve, and means for preventing the passage of liquid fluid through the alternate fluid conduit, and yet permitting the passage of gaseous fluid therethrough.

23. A system as set forth in claim 22, wherein the means for preventing the passage of liquid fluid through the alternate fluid conduit and yet permitting the passage of gaseous fluid therethrough, comprises a Porex-type plug.

24. A system as set forth in claim 11, wherein the restricting means includes a capillary-like fluid pathway through which the medication must pass before entering the pump.

25. A system as set forth in claim 24, wherein the capillary-like fluid pathway comprises a length of capillary tubing having an inlet end in fluid communication with the reservoir and the medication receiving means, and an outlet end in fluid communication with the pumping chamber.

26. A system as set forth in claim 25, wherein the capillary tubing is wound about a spool and situated within a rigid housing.

27. A system as set forth in claim 25, wherein the capillary tubing inlet is positioned within a Bifurcation Valve which permits medication to flow freely between the reservoir, the medication receiving means, and the capillary tubing inlet.

28. A subcutaneously implantable medication infusion control assembly having a medicament recharge restriction, comprising:
an injection port for receiving medication into the assembly by injection, including:
an elastomeric outer housing including an integral elastomeric septum;
a first base member situated within the outer housing and contiguously engaging a peripheral flange of the septum;
a second base member situated within the first base member and the outer housing, the second base member contiguously engaging the peripheral flange of the septum opposite the first base member such that the septum is compressed between the first and second base members, wherein the second base member and the septum define an internal chamber;
a filter barrier supported by the second base member, the filter barrier separating the internal chamber into an upper portion adjacent to the septum and a lower portion; and an outlet extending from the lower portion of the internal chamber exteriorly through the outer housing;

a self-recharging, manually actuable pump for discharging a measured amount of medication from a pumping chamber;

a capillary-like fluid pathway for conducting pump recharge medication into the pumping chamber, the capillary-like fluid pathway including a length of capillary tubing having an inlet end in fluid communication with recharge medication injected into the assembly, and an outlet end in fluid communication with the pumping chamber, the capillary tubing effectively limiting the amount of recharge medication permitted to enter into the pumping chamber over a given period of time;

a primary fluid conduit for conducting discharge medication from the pumping chamber; and valve means for controlling the flow of discharge medication through the primary fluid conduit, the valve means including a normally closed valve actuable by manual percutaneous manipulation, and a one-way valve situated within the primary fluid conduit between the pumping chamber and the normally closed valve, wherein the normally closed valve includes a resiliently flexible body which defines a fluid flow passageway therethrough, a valve member positioned within the fluid flow passageway to occlude the normally closed valve, a valve inlet in fluid communication with the primary fluid conduit, a valve outlet, a valve passageway situated between the valve inlet and the valve outlet, wherein the valve member is resiliently biased to occlude the valve passageway, and a displacement finger situated and configured to displace the valve member and open the normally closed valve to fluid flow therethrough when the normally closed valve is actuated by manual percutaneous manipulation.

29. A subcutaneously implantable medication infusion control assembly having a medicament recharge restriction, comprising:

an injection port for receiving medication into the assembly by injection;

a self-recharging, manually actuable pump for discharging a measured amount of medication from a pumping chamber;

a capillary-like fluid pathway for conducting pump recharge medication into the pumping chamber, the capillary-like fluid pathway including a length of capillary tubing having an inlet end in fluid communication with recharge medication injected into the assembly, and an outlet end in fluid communication with the pumping chamber, the capillary tubing effectively limiting the amount of recharge medication permitted to enter into the pumping chamber over a given period of time, wherein the capillary tubing is wound about a spool and situated within a rigid housing, and wherein the capillary tubing inlet is positioned within a bifurcation valve;

a primary fluid conduit for conducting discharge medication from the pumping chamber; and valve means for controlling the flow of discharge medication through the primary fluid conduit, the valve means including a normally closed valve actuable by manual percutaneous manipulation, and a one-way valve situated within the primary fluid conduit between the pumping chamber and the normally closed valve.

30. A subcutaneously implantable medication infusion control assembly having a medicament recharge restriction, comprising:

an injection port for receiving medication into the assembly by injection;

a self-recharging, manually actuable pump for discharging a measured amount of medication from a pumping chamber;

a capillary-like fluid pathway for conducting pump recharge medication into the pumping chamber, the capillary-like fluid pathway including a length of capillary tubing having an inlet end in fluid communication with recharged medication injected into the assembly, and an outlet end in fluid communication with the pumping chamber, the capillary tubing effectively limiting the amount of recharge medication permitted to enter into the pumping chamber over a given period of time;

a primary fluid conduit for conducting discharge medication from the pumping chamber;

valve means for controlling the flow of discharge medication through the primary fluid conduit, the valve means including a normally closed valve actuable by manual percutaneous manipulation, and a one-way valve situated within the primary fluid conduit between the pumping chamber and the normally closed valve; and means for bypassing the primary fluid conduit, the bypassing means permitting steam autoclave sterilization of the pumping chamber through the normally closed valve, and yet disallowing the flow of liquid fluid through the bypassing means.

31. A control assembly as set forth in claim 30, wherein the bypassing means includes an alternate fluid conduit extending between the pumping chamber and the normally closed valve, and means for preventing the passage of liquid fluid through the alternate fluid conduit, and yet permitting the passage of gaseous fluid therethrough.

32. A control assembly as set forth in claim 31, wherein the means for preventing passage of liquid fluid through the alternate fluid conduit, and yet permitting the passage of gaseous fluid therethrough, comprises a Porex-type plug.

* * * * *

UNITED STATES PATENT AND TRADEMARK OFFICE
CERTIFICATE OF CORRECTION

PATENT NO. : 5,085,644
DATED : February 4, 1992
INVENTOR(S) : David A. Watson and Mark J. Licata It is certified that error appears in the above-identified patent and that said Letters Patent is hereby corrected as shown below:

In column 11, line 38, delete "a" and insert therefor --A--.

In column 16, line 2, delete "conduct" and insert therefor --conduit--.

In column 18, line 15, delete the word "controlling".

Signed and Sealed this

Eighth Day of June, 1993

Attest:

MICHAEL K. KIRK

Attesting Officer      Acting Commissioner of Patents and Trademarks